(12) United States Patent
Usui et al.

(10) Patent No.: US 7,848,568 B2
(45) Date of Patent: Dec. 7, 2010

(54) MEDICINE BAG AND COLOR REPRODUCTION SYSTEM

(75) Inventors: Nobuaki Usui, Kahoku (JP); Hironori Kouno, Kahoku (JP)

(73) Assignee: PFU Limited, Ishikawa (JP)

(*) Notice: Subject to any disclaimer, the term of this patent is extended or adjusted under 35 U.S.C. 154(b) by 1076 days.

(21) Appl. No.: 11/588,409

(22) Filed: Oct. 27, 2006

(65) Prior Publication Data

US 2007/0230832 A1    Oct. 4, 2007

(30) Foreign Application Priority Data

Apr. 3, 2006    (JP)    .......................... P2006-101436

(51) Int. Cl.
*G06K 9/00*    (2006.01)
*G03F 3/08*    (2006.01)

(52) U.S. Cl. ..................................... 382/165

(58) Field of Classification Search ......... 382/162–167; 358/1.9, 515.518, 530; 345/589, 600–604; 383/4

See application file for complete search history.

(56) References Cited

U.S. PATENT DOCUMENTS

| | | | | |
|---|---|---|---|---|
| 5,414,537 | A * | 5/1995 | Omuro et al. ............... | 358/518 |
| 5,852,675 | A | 12/1998 | Matsuo et al. | |
| 6,115,138 | A * | 9/2000 | Yanaka ........................ | 358/1.9 |
| 6,853,747 | B1 * | 2/2005 | Matsuura et al. ............ | 382/167 |
| 7,162,079 | B2 * | 1/2007 | Tamagawa ................... | 382/167 |
| 7,202,971 | B2 * | 4/2007 | Okamoto .................... | 358/1.9 |
| 7,277,200 | B2 * | 10/2007 | Ohga ......................... | 358/1.9 |
| 7,382,490 | B2 * | 6/2008 | Lammens et al. ............ | 358/1.9 |
| 2005/0219566 | A1 * | 10/2005 | Sugita ........................ | 358/1.9 |
| 2007/0230832 | A1 * | 10/2007 | Usui et al. .................... | 383/4 |

FOREIGN PATENT DOCUMENTS

JP    2003-134526    5/2003

OTHER PUBLICATIONS

Office Action issued on Feb. 5, 2009 in corresponding German Patent Application 10 2006 050 485.2-52.

* cited by examiner

*Primary Examiner*—Amir Alavi

(57) ABSTRACT

A color reproduction system using a medicine bag including a bag adapted to accommodate a medicine therein, and a color chart provided on an outer surface of the bag. The medicine bag includes a first medicine bag having a first color chart and located at a first location and a second medicine bag having a second color chart and located at a second location remote from the first location. The color reproducing system includes: a first device, located at the first location, and operable to read the first color chart so as to generate first color data; and a second device, located at the second location, and operable to transmit image data of an object and second color data of the second color chart to the first device. The first device corrects the image data by using a correction value based on the first color data and the second color data, and displays the corrected image data.

3 Claims, 2 Drawing Sheets

MEDICINE BAG AND COLOR REPRODUCTION SYSTEM

BACKGROUND OF THE INVENTION

The present invention relates to an art which, in a geographically remote condition such as telemedicine (including barbering and cosmetology such as cosmetic surgery), in a case of inputting an image by means of an image input device, and reproducing the image by means of an image output device, corrects a phenomenon in which the image is reproduced in a different color due to differences in device characteristics, photographing environmental characteristics (such as an illumination) etc., and color-reproduces the image correctly between remote locations.

Telemedicine has been practiced in which a doctor diagnoses a patient in a geographically remote location by examining his or her complexion displayed on a monitoring device on the doctor side by means of a communication between image devices installed in their respective locations.

In a case of carrying out such a remote diagnosis, in some cases, the patient's complexion displayed on the monitoring device on the doctor side has been displayed differing from an actual patient's complexion due to differences in color properties of image input and output devices (monitoring devices), and environmental characteristics, such as an illumination in a location in which the patient is photographed.

As a color reproduction for correcting such a difference in color and displaying a correct color, a method has been proposed by which the patient side and the doctor side have identical color charts for color reproduction, and the color reproduction is carried out by making a correction for a color matching between a color chart obtained by displaying the identical color chart on the monitoring device and the color chart the doctor actually has at hand (refer to JP-A-2003-134526).

However, in order to use such a method, it is necessary that the patient side and the doctor side never fail to have the identical color charts for the color reproduction and, normally, the color charts use special ink and papers in order to prevent a discoloration so that those are very expensive, sometimes, several hundred thousand yen or more each, so there has been a problem resulting in expensive telemedical facilities in the event of a large number of patients.

SUMMARY

It is therefore an object of the invention to provide, in a telemedical field (including barbering and cosmetology such as cosmetic surgery), a color reproduction on image input and output devices between remote locations at a low price.

In order to achieve the object, according to the invention, there is provided a medicine bag comprising:

a bag, adapted to accommodate a medicine therein; and
a color chart, provided on an outer surface of the bag.

According to the invention, there is provided a color reproduction system using the medicine bag, the medicine bag that includes a first medicine bag having a first color chart and located at a first location and a second medicine bag having a second color chart and located at a second location remote from the first location, the color reproducing system comprising:

a first device, located at the first location, and operable to read the first color chart so as to generate first color data; and a second device, located at the second location, and operable to transmit image data of an object and second color data of the second color chart to the first device, wherein the first device corrects the image data by using a correction value based on the first color data and the second color data, and displays the corrected image data.

The correction value may be based on color data of gray of both the first color data and the second color data.

DETAIL DESCRIPTION OF PREFERRED EMBODIMENTS

A description will be given, with reference to the drawings, of a representative example according to the invention. Hereafter, identical parts are indicated by identical numerals, and a detailed description may be omitted.

A patient 4 receiving a telemedicine, when receiving a medicine at a prescribed frequency (normally every two weeks), receives a color-charted medicine bag 1 having a color chart printed in a normally unprinted space on its back or the like, as well as the medicine.

In order for the patient 4 to obtain an accurate diagnosis in a remote location, a doctor 5 has to accurately identify tones of a skin color which is a complexion of the patient 4.

Figure 1:
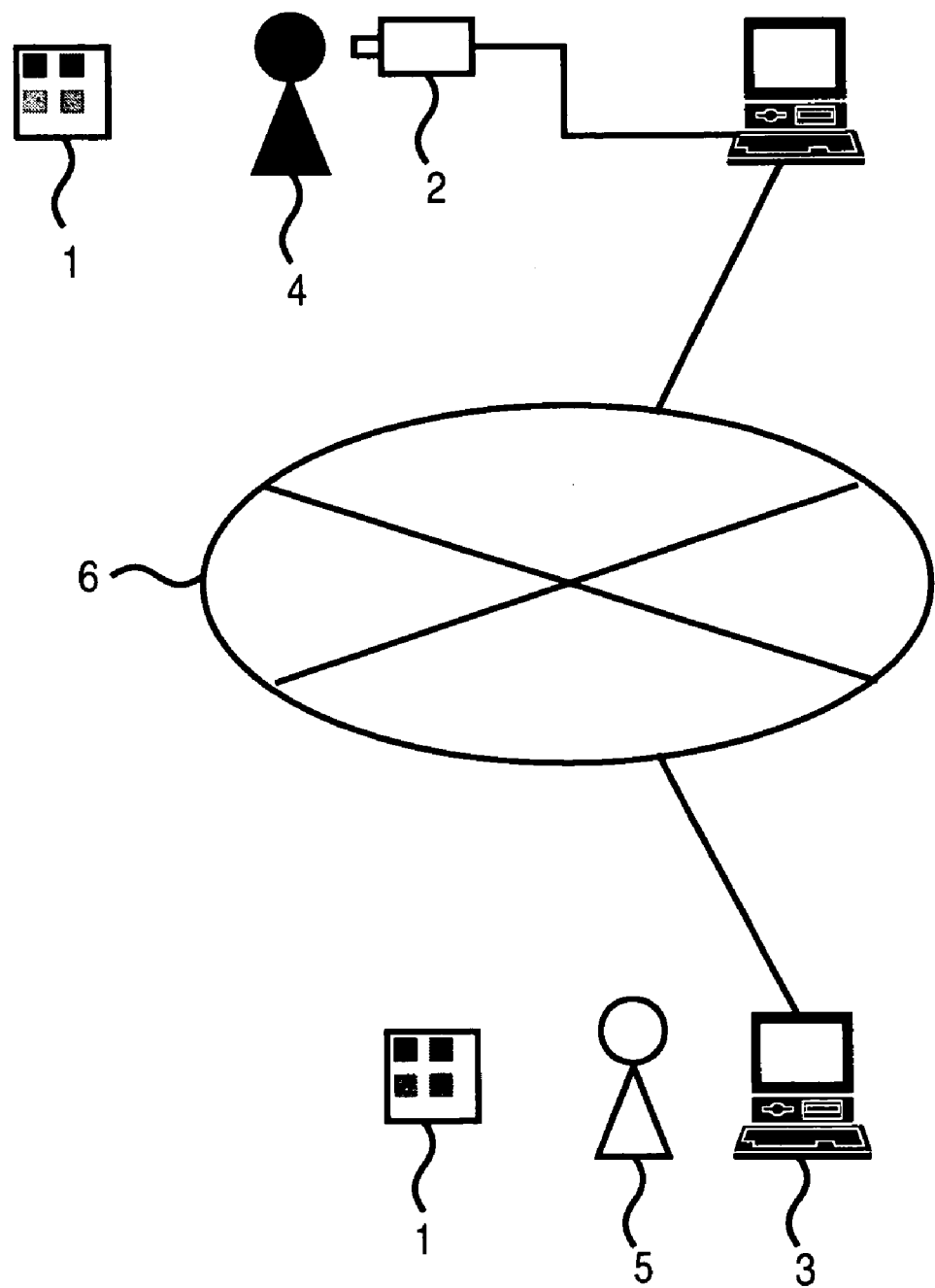
FIG. 1 is an overall configuration diagram of the invention.

As shown in FIG. 1, the patient 4 receiving the telemedicine photographs his or her own image by means of an image input device 2, and communicates the image by way of a network 6, causing it to be displayed on an image output device 3 installed on the doctor 5 side.

Although the doctor 5 makes a diagnosis by examining a condition of the patient 4 displayed on the image output device 3, an actual color of the patient 4 and a color of the patient 4 displayed on the image output device 3 may differ from one another due to color properties of the image input device 2 and the image output device 3, and environmental characteristics, such as an illumination in a location in which the patient 4 is photographed.

Accordingly, in practicing the telemedicine, a color reproduction is carried out as described hereafter before the diagnosis.

Figure 2:
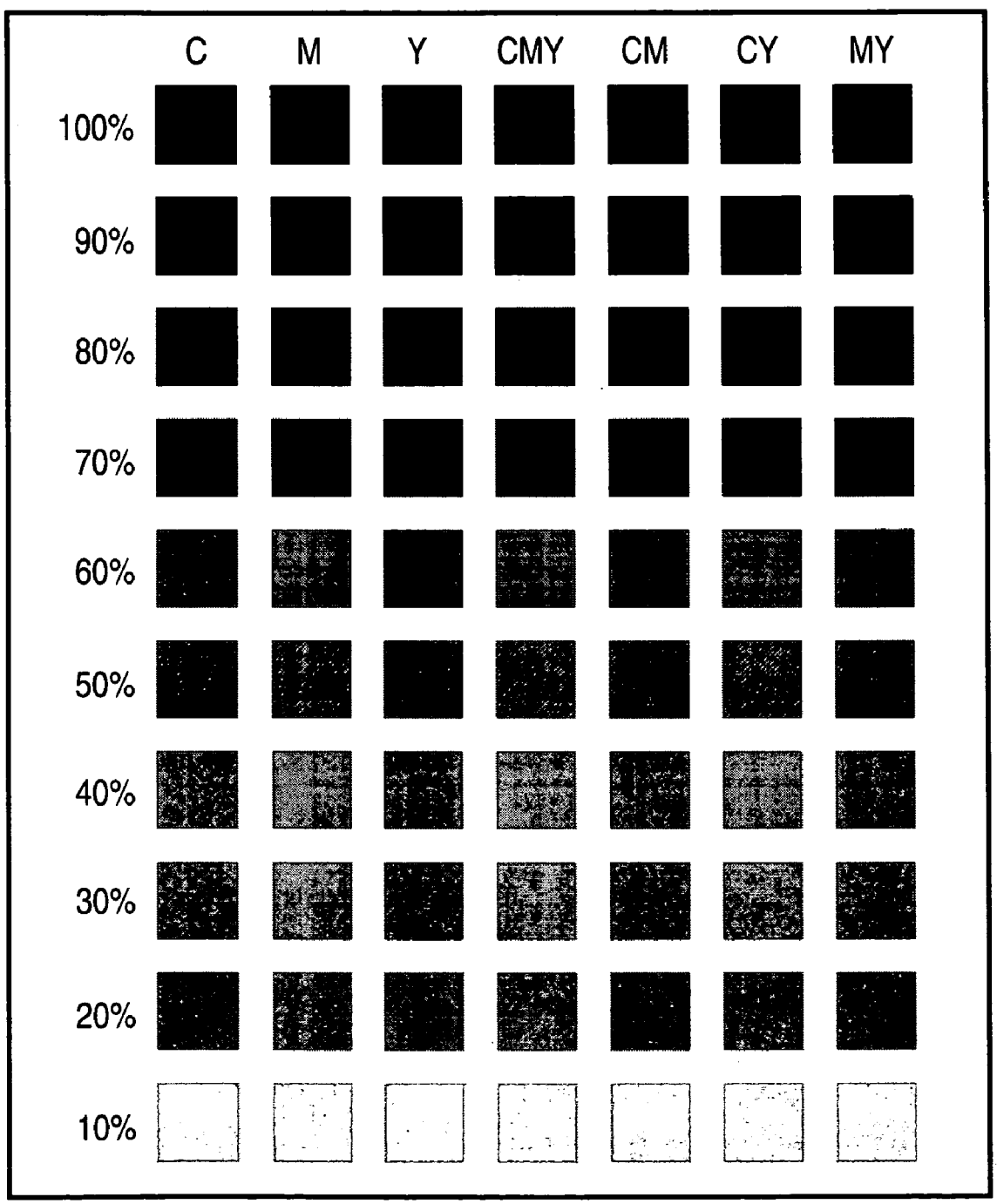
FIG. 2 is an example of a color chart printed on a color-charted medicine bag.

The color chart on the color-charted medicine bag 1 is caused to be displayed on the image output device 3 installed on the doctor 5 side. As the color chart, as shown in FIG. 2, it is also acceptable to previously print each patch in which a density of each color, C (cyan), M (magenta), Y (yellow), CMY (gray), CM (blue), CY (green) and MY (red), is varied in ten stages.

The doctor 5 calculates a difference between darkest patch information and brightest patch information, and verifies whether or not each item of patch information maintains an identifiable dynamic range.

In the event that the dynamic range is fully maintained, a brightness is increased and decreased in such a way that patches having a density of 50% and 60% representing central patches occupy an intermediate position, and a contrast is adjusted in such a way that a darkest patch and a brightest patch fall within an appropriate range.

A correction parameter for such an automatic correction is expressed by the following equation. An RGB value of each gray pattern to be color-converted is indicated by x, an RGB value color-converted is indicated by y, and the contrast and the brightness are set at a range of from −127 to +128.

$$y = x + \text{brightness} - \text{contrast} * \cos(3.141592 * x/256) + 0.5,$$
$$\text{wherein } y = \min(255, y) \text{ and } y = \max(0, y).$$

Eventually, a visual confirmation is made, and a density of each patch is adjusted by an adjustment on the image output device 3 and an increase and decrease of the correction parameter in such a way that the density can appropriately be identified.

After the adjustment, the doctor 5 carries out a color production, particularly, a color production processing of a skin color, such as a complexion important for a diagnosis in the telemedicine, using the color chart on the color-charted medicine bag 1 of the patient 4, displayed on the image output device 3, and the color chart of the color-charted medicine bag 1 at hand.

This color reproduction method, being a polynomial approximation technique, uses a 3×3 determinant to be described hereafter.

$$\begin{pmatrix} d1 \\ d2 \\ d3 \end{pmatrix} = \begin{pmatrix} c11 & c12 & c13 \\ c21 & c22 & c23 \\ c31 & c32 & c33 \end{pmatrix} \begin{pmatrix} s1 \\ s2 \\ s3 \end{pmatrix}$$

An RGB value of gray patches in the color chart on the color-charted medicine bag 1 of the patient 4, displayed on the image output device 3 of the doctor 5, being indicated by S=(s1, s2, s3), an RGB value of gray patches in the color chart on the color-charted medicine bag 1 the doctor 4 has at hand, indicated by D=(d1, d2, d3), and a 3×3 color reproduction matrix, indicated by C, a color reproduction conversion is carried out using the heretofore described determinant.

In order to calculate a color reproduction parameter of the matrix C, an optimization by the following equation is carried out.

$$E = \frac{1}{10} \sum_{i=1}^{10} |Di - C \cdot Si|$$

i indicating an ID for identifying each gray patch (i=1, 2, ... 10), and E indicating a mean error, the matrix C minimizing E is obtained by a least squares method.

After the color reproduction parameter of the matrix C is calculated, by carrying out an image conversion using the color reproduction parameter as a color correction parameter of the image output device 3, the image displayed on the image output device 3 of the doctor 5 can be used as a color-reproduced image of the actual complexion or the like of the patient 4, making it possible to carry out a correct diagnosis from a remote location.

By using the heretofore described color production system, it is possible for the patient 4 and the doctor 5 to prepare identical color charts at a low price, making it possible to carry out a practical and economical telemedicine.

According to an aspect of the invention, as a hospital provides the patient with a medicine bag together with a medicine at least once every two weeks, it is assured that the color chart is constantly in a new condition. So that, by printing the color chart in an unprinted space on the back or the like of the medicine bag, the patient and the doctor can prepare identical color charts at a low price with no need to use special ink which does not discolor or deteriorate over a long period and, by carrying out a color reproduction using the color charts, it becomes possible to realize telemedicine at a low price.

According to an aspect of the invention, it is possible to carry out the color reproduction correctly without being effected by color properties of the image input and output devices used in the telemedicine, and environmental characteristics, such as an illumination in a location in which the patient is present.

Also, according to an aspect of the invention, by making mainly a correction for a color matching of gray patches in the color chart, it becomes possible to carry out an accurate color reproduction for a skin color which is a complexion, on which a particularly accurate color reproduction has to be carried out in the telemedical field.

What is claimed is:

1. A medicine bag provided to a remote patient prior to a telemedicine consultation, comprising:
    a bag, adapted to accommodate a medicine therein; and
    a color chart, including a two dimensional array of colored patches having various color density and brightness characteristics, provided on an outer surface of the bag,
        wherein a colored image of the patient at the time of the consultation is corrected based on the two dimensional array of colored patches which is included in the colored image.

2. A color reproduction system using a first medicine bag having a first color chart and being located at a first location and a second medicine bag having a second color chart and being located at a second location remote from the first location, the color reproducing system comprising:
    a first device, located at the first location, and operable to generate first color data based on the first color chart; and
    a second device, located at the second location, and operable to transmit image data of an object and second color data based on the second color chart to the first device, wherein
    the first color chart and the second color chart include the same plurality of patches having various color density and brightness characteristics, and
    the first device corrects the image data by determining and applying correction values based on the first color data and the second color data, and displays the corrected image data.

3. The color reproduction system according to claim 2, wherein
    the correction values are determined based on color data of gray patches of both the first color data and the second color data.

* * * * *